US012778916B2

(12) United States Patent
Lee et al.

(10) Patent No.: US 12,778,916 B2
(45) Date of Patent: Nov. 3, 2026

(54) PHARMACEUTICAL COMPOSITION FOR PREVENTION, ALLEVIATION OR TREATMENT OF SARCOPENIA, CONTAINING ROR-α ACTIVATOR JC1-40

(71) Applicant: SEOUL NATIONAL UNIVERSITY R & DB FOUNDATION, Seoul (KR)

(72) Inventors: Mi-Ock Lee, Seoul (KR); Hyeung-Geun Park, Seoul (KR); Hyeon-Ji Kim, Seoul (KR)

(73) Assignee: SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 318 days.

(21) Appl. No.: 18/511,106

(22) PCT Filed: May 13, 2022

(86) PCT No.: PCT/KR2022/006925
§ 371 (c)(1),
(2) Date: Nov. 16, 2023

(87) PCT Pub. No.: WO2022/245067
PCT Pub. Date: Nov. 24, 2022

(65) Prior Publication Data

US 2025/0082592 A1 Mar. 13, 2025

(30) Foreign Application Priority Data

May 17, 2021 (KR) ........................ 10-2021-0063110
May 12, 2022 (KR) ........................ 10-2022-0058534

(51) Int. Cl.
*A61K 31/17* (2006.01)
*A61P 21/00* (2006.01)

(52) U.S. Cl.
CPC .............. *A61K 31/17* (2013.01); *A61P 21/00* (2018.01)

(58) Field of Classification Search
CPC ................................ A61K 31/17; A61P 21/00
See application file for complete search history.

(56) References Cited

U.S. PATENT DOCUMENTS

2018/0265462 A1* 9/2018 Lee ....................... C07C 335/12

FOREIGN PATENT DOCUMENTS

KR 101771680 8/2017
KR 20210005880 1/2021

OTHER PUBLICATIONS

Machine Translation, Kyu et al., Pharmaceutical composition for prevention or treatment of cancer comprising ROR activating regulator, KR20160132534A, Nov. 21, 2016; Machine Translation obtained from USPTO STIC Translation Services (Year: 2016).*
Beaudart et al., Health outcomes of sarcopenia: a systematic review and meta-analysis, PLoSONE, 2017, 12, 1, e0169548 (Year: 2017).*
A. J. Cruz-Jentoft, A. A. Sayer, Sarcopenia, Lancet 2019, 393, 2636-2646 (Year: 2019).*
Kim et al., Liver-specific deletion of RORa aggravates diet-induced nonalcoholic steatohepatitis by inducing mitochondrial dysfunction, Scientific reports 2017, 7, 16041 (Year: 2017).*
Jung et al., Sarcopenia in youth, Metabolism 2023, 144, 155557 (Year: 2023).*
J. M. Kim. Building a tiered approach to in vitro predictive toxicity screening, combo chemical high throughput screening 2010, 13, 188-206 (Year: 2010).*
Anton M. Jetten, Hong Soon Kang, Yukimasa Takeda, "Retinoic acid-related orphan receptors α and γ: key regulators of lipid/glucose metabolism, inflammation, and insulin sensitivity", Frontiers in Endocrinology, vol. 4, doi:10.3389/fendo.2013.00001, pp. 1-8, XP055159436.
Azuma Kotaro, Ikeda Kazuhiro, Inoue Satoshi, "Functional Mechanisms of Mitochondrial Respiratory Chain Supercomplex Assembly Factors and Their Involvement in Muscle Quality", International Journal of Molecular Sciences, vol. 21, No. 3182, doi:10.3390/ijms21093182, pp. 1-17, XP093007574.
Kim Hyeon-Ji, Han Yong-Hyun, Na Hyelin, Kim Ju-Yeon, Kim Taewook, Kim Hye-Jin, Shin Chanseok, Lee Jung Weon, Lee Mi-Ock, "Liver-specific deletion of RORa aggravates diet-induced nonalcoholic steatohepatitis by inducing mitochondrial dysfunction", Scientific Reports, (Dec. 1, 2017), vol. 7, No. 16041, doi:10.1038/s41598-017-16077-y, pp. 1-11, XP093007559.

* cited by examiner

*Primary Examiner* — James H Alstrum-Acevedo
*Assistant Examiner* — Allen Chao
(74) *Attorney, Agent, or Firm* — Riverside Law LLP

(57) ABSTRACT

The present invention relates to a pharmaceutical composition for the prevention, alleviation or treatment of sarcopenia, containing a RORα activator JC1-40. A composition according to the present invention increases mitochondrial membrane potential, the number of mitochondria, and the expression or activity of mitochondria-related genes or proteins to thus increase biosynthesis of mitochondria, and is thus expected to be effective in the prevention, alleviation and treatment of sarcopenia.

7 Claims, 9 Drawing Sheets

Specification includes a Sequence Listing.

```
SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: SDHA Forward Primer

<400> SEQUENCE: 1

gaaaggcggg caggctcatc                                                  20


<210> SEQ ID NO 2
<211> LENGTH: 21
<212> TYPE: DNA
<213> ORGANISM: Artificial Sequence
<220> FEATURE:
<223> OTHER INFORMATION: SDHA Reverse Primer

<400> SEQUENCE: 2

caccacggca ctccccattt t                                                21


<210> SEQ ID NO 3
<211> LENGTH: 24
<212> TYPE: DNA
<213> ORGANISM: Artificial Sequence
<220> FEATURE:
<223> OTHER INFORMATION: COX5A Forward Primer

<400> SEQUENCE: 3

ttgatgcctg ggaattgcgt aaag                                             24


<210> SEQ ID NO 4
<211> LENGTH: 23
<212> TYPE: DNA
<213> ORGANISM: Artificial Sequence
<220> FEATURE:
```

-continued

```
<223> OTHER INFORMATION: COX5A Reverse Primer

<400> SEQUENCE: 4

aacaacctcc aagatgcgaa cag                                              23


<210> SEQ ID NO 5
<211> LENGTH: 26
<212> TYPE: DNA
<213> ORGANISM: Artificial Sequence
<220> FEATURE:
<223> OTHER INFORMATION: MCAD Forward Primer

<400> SEQUENCE: 5

gatcgcaatg ggtgcttttg atagaa                                           26


<210> SEQ ID NO 6
<211> LENGTH: 26
<212> TYPE: DNA
<213> ORGANISM: Artificial Sequence
<220> FEATURE:
<223> OTHER INFORMATION: MCAD Reverse Primer

<400> SEQUENCE: 6

agctgattgg caatgtctcc agcaaa                                           26


<210> SEQ ID NO 7
<211> LENGTH: 19
<212> TYPE: DNA
<213> ORGANISM: Artificial Sequence
<220> FEATURE:
<223> OTHER INFORMATION: PGC-1-alpha Forward Primer

<400> SEQUENCE: 7

ccctgccatt gttaagacc                                                   19


<210> SEQ ID NO 8
<211> LENGTH: 19
<212> TYPE: DNA
<213> ORGANISM: Artificial Sequence
<220> FEATURE:
<223> OTHER INFORMATION: PGC-1-alpha Reverse Primer

<400> SEQUENCE: 8

tgctgctgtt cctgttttc                                                   19


<210> SEQ ID NO 9
<211> LENGTH: 24
<212> TYPE: DNA
<213> ORGANISM: Artificial Sequence
<220> FEATURE:
<223> OTHER INFORMATION: NRF-1 Forward Primer

<400> SEQUENCE: 9

cccccgagga cacttcttat gatg                                             24


<210> SEQ ID NO 10
<211> LENGTH: 24
<212> TYPE: DNA
<213> ORGANISM: Artificial Sequence
<220> FEATURE:
<223> OTHER INFORMATION: NRF-1 Reverse Primer

<400> SEQUENCE: 10

ggccgtttcc gtttcttccc tgtt                                             24
```

-continued

```
<210> SEQ ID NO 11
<211> LENGTH: 21
<212> TYPE: DNA
<213> ORGANISM: Artificial Sequence
<220> FEATURE:
<223> OTHER INFORMATION: NRF-2-alpha Forward Primer

<400> SEQUENCE: 11

caagagcaac agatgaatga g                                              21


<210> SEQ ID NO 12
<211> LENGTH: 22
<212> TYPE: DNA
<213> ORGANISM: Artificial Sequence
<220> FEATURE:
<223> OTHER INFORMATION: NRF-2-alpha Reverse Primer

<400> SEQUENCE: 12

actttaatcg tagtcggtgt ag                                             22


<210> SEQ ID NO 13
<211> LENGTH: 21
<212> TYPE: DNA
<213> ORGANISM: Artificial Sequence
<220> FEATURE:
<223> OTHER INFORMATION: TFAM Forward Primer

<400> SEQUENCE: 13

ggaatgtgga gcgtgctaaa a                                              21


<210> SEQ ID NO 14
<211> LENGTH: 21
<212> TYPE: DNA
<213> ORGANISM: Artificial Sequence
<220> FEATURE:
<223> OTHER INFORMATION: TFAM Reverse Primer

<400> SEQUENCE: 14

acaagactga tagacgaggg g                                              21
```

PHARMACEUTICAL COMPOSITION FOR PREVENTION, ALLEVIATION OR TREATMENT OF SARCOPENIA, CONTAINING ROR-α ACTIVATOR JC1-40

CROSS-REFERENCE TO RELATED APPLICATIONS

This application is a U.S. national phase application filed under 35 U.S.C. § 371 claiming benefit to International Patent Application No. PCT/KR2022/006925, filed on May 13, 2022, which claims priority to Korean Application No. 10-2021-0063110, filed on May 17, 2021, and Korean Application No. 10-2022-0058534, filed on May 12, 2022, the disclosures of each of which are incorporated by reference herein in their entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206132-0162-00US_SequenceListing.txt" in ASCII format, which was created on Nov. 16, 2023, and is 3,280 bytes in size.

TECHNICAL FIELD

The present invention relates to a pharmaceutical composition for preventing, improving, or treating sarcopenia, comprising RORα activator JC1-40, and the like.

BACKGROUND ART

South Korean society is facing an era of an ultra-aged society due to the extension of average life expectancy and a decrease in birthrate. Moreover, obesity, which is a major threat to the health of modern society, is continuously increasing in South Korean society, serving as a cause of various chronic diseases and inducing an increase in premature deaths. As one of the physical changes due to aging and obesity, sarcopenia and sarcopenic obesity, which appear as a decrease in muscle mass and strength, not only cause the loss of mobility in daily life but also may lead to chronic liver disease, cardiovascular disease, lung disease, brain disease, and degenerative diseases, hence being a disease that must be overcome for the health of humanity in modern society. Currently, calorie restriction, protein supplementation, and exercise therapy have become primary treatment methods, and testosterone, myostatin inhibitors, ghrelin analogs, and vitamin K are being suggested as future treatment methods. However, drugs specifically treating sarcopenia are still absent.

Mitochondria are cellular organelles central to energy metabolism, and the quantitative and qualitative maintenance of the mitochondria is an essential factor for maintaining intracellular homeostasis. Mitochondrial function regulation occurs mainly through biosynthesis, fission/fusion, and mitochondrial-specific autophagic actions. The functional damage of mitochondria is a major factor contributing to the complex pathogenesis of sarcopenia, such as oxidative stress, cell death, inflammation and so on.

RORα (also known as NR1F1, RORA, or RZR) is a member of the steroid hormone receptor superfamily and a transcription factor that regulates gene expression. RORα is regulated through the specific binding of ligands such as cholesterol and its derivatives, melatonin, and CGP52608, one of the thiazolidinediones, and controls the expression of target genes by binding to the ROR-response element (RORE) in the promoter of the target genes. In muscle, RORα promotes muscle differentiation through direct interaction with p300 and MyoD. RORα deficient mice (sg/sg, sg/+) exhibited improved glucose intolerance and increased insulin sensitivity, suggesting the potential involvement of muscle RORα in glucose metabolism. Furthermore, when the expression of RORα in muscles was reduced, the expression of genes related to lipid homeostasis (caveolin-3, CPT-1) decreased, and transgenic mice exhibiting muscle-specific expression of truncated (dominant negative) RORα1 demonstrated that RORα might be involved in lipid homeostasis through regulation of the Akt2-AMPK pathway. Additionally, 50 when RORα was activated in muscle cells through synthetic activators and natural substances, expression of fibroblast growth factor 21 (FGF21), activation of mitochondrial complex II, and formation of supercomplexes were increased, implying the applicability of RORα activity in the treatment of obesity-related diseases and sarcopenia. 55 Thus, the inventors of the present invention have confirmed that the compound JC1-40 increases mitochondrial biosynthesis and enhances the expression of mitochondrial regulation factors, thereby completing the present invention.

DISCLOSURE

Technical Problem

The inventors of the present invention have confirmed that the compound JC1-40 increases mitochondrial biosynthesis and enhances the expression of mitochondrial regulation factors, thereby completing the present invention.

The present invention is directed to provide a pharmaceutical composition for preventing or treating sarcopenia, comprising JC1-40 or a pharmaceutically acceptable salt thereof as an active ingredient.

The present invention is also directed to provide a food composition for preventing or improving sarcopenia, comprising JC1-40 or a food acceptable salt thereof as an active ingredient.

Moreover, the present invention is directed to provide a cosmetic composition for improving muscular function, comprising JC1-40 or a cosmetically acceptable salt thereof as an active ingredient.

In addition, the present invention is directed to provide a composition for increasing mitochondrial biosynthesis, comprising JC1-40 or a pharmaceutically acceptable salt thereof as an active ingredient.

However, the technical problem that the present invention seeks to solve is not limited to the problems mentioned above, and other unmentioned problems will be clearly understood by those skilled in the art from the description below.

Technical Solution

To achieve the purpose of the present invention, the present invention provides a pharmaceutical composition for preventing or treating sarcopenia, comprising JC1-40 or a pharmaceutically acceptable salt thereof as an active ingredient.

Furthermore, the present invention provides a food composition for preventing or improving sarcopenia, comprising JC1-40 or a food acceptable salt thereof as an active ingredient.

Moreover, the present invention provides a cosmetic composition for improving muscular function, comprising JC1-40 or a cosmetically acceptable salt thereof as an active ingredient.

Additionally, the present invention provides a composition for increasing mitochondrial biosynthesis, comprising JC1-40 or a pharmaceutically acceptable salt thereof as an active ingredient.

In one embodiment of the present invention, the JC1-40 may be an activator of RORα protein, but is not limited thereto.

In another embodiment of the present invention, the JC1-40 may be included at a concentration of 1 to 100 μM relative to the total composition, but is not limited thereto.

In yet another embodiment of the present invention, the JC1-40 may satisfy at least one of the followings, but is not limited thereto: a) increasing mitochondrial membrane potential; b) increasing mitochondrial quantity; and c) increasing mitochondrial biosynthesis.

In yet another embodiment of the present invention, the JC1-40 may increase the expression or activity of a gene or protein selected from the group consisting of SDHA, COX5A, MCAD, PGC-1α, NRF1, NRF2α, and TFAM, but is not limited thereto.

In yet another embodiment of the present invention, the expression or activity of the TFAM gene or protein may be dependent on RORα, but is not limited thereto.

In yet another embodiment of the present invention, the sarcopenia may be obese sarcopenia or senile sarcopenia, but is not limited thereto.

Additionally, the present invention provides a method for preventing or treating sarcopenia, comprising the step of administering JC1-40 or a pharmaceutically acceptable salt thereof to a subject in need thereof.

Furthermore, the present invention provides a use of JC1-40 or a pharmaceutically acceptable salt thereof for preventing or treating sarcopenia.

Moreover, the present invention provides a use of JC1-40 or a pharmaceutically acceptable salt thereof for producing a drug for preventing or treating sarcopenia.

In addition, the present invention provides a method for increasing mitochondrial biosynthesis, comprising the step of administering JC1-40 or a pharmaceutically acceptable salt thereof to a subject in need thereof.

Moreover, the present invention provides a use of JC1-40 or a pharmaceutically acceptable salt thereof for increasing mitochondrial biosynthesis.

Additionally, the present invention provides a use of JC1-40 or a pharmaceutically acceptable salt thereof for producing a drug for increasing mitochondrial biosynthesis.

Moreover, the present invention provides a method for improving muscular function, comprising the step of administering JC1-40 or a salt thereof to a subject in need thereof.

Additionally, the present invention provides a use of JC1-40 or a salt thereof for improving muscular function.

Furthermore, the present invention provides a use of JC1-40 or a cosmetically acceptable salt thereof for producing a cosmetic utilized for improving muscular function.

Advantageous Effects

The composition according to the present invention is anticipated to be effective in preventing, improving, and treating sarcopenia by increasing mitochondrial membrane potential, enhancing the quantity of mitochondria, and elevating the expression or activity of genes or proteins related to mitochondria, thereby augmenting mitochondrial biosynthesis.

BEST MODES OF THE INVENTION

Figure 1:
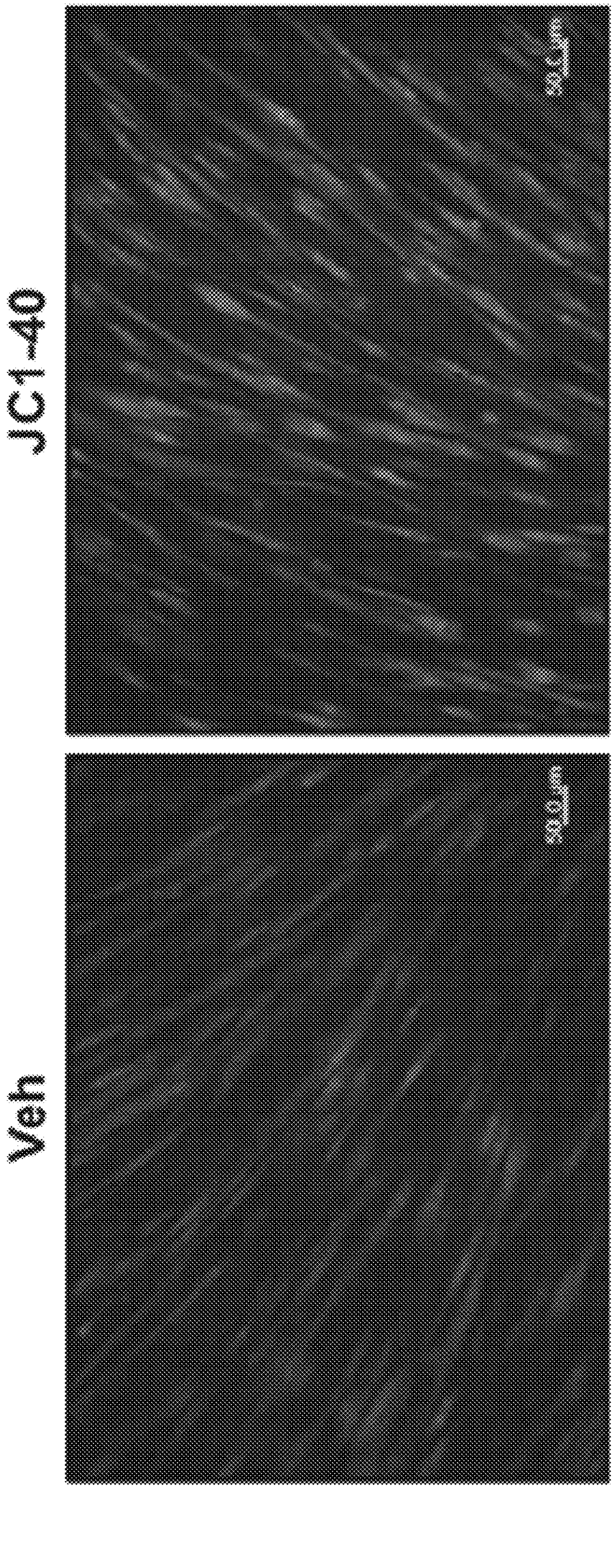
FIG. 1 shows the effect of JC1-40 on mitochondrial membrane potential in C2C12 cells.

In a devoted effort to develop a drug that effectively treats sarcopenia or decelerates its progression, the inventors of the present invention have achieved the completion of the present invention by confirming that the compound JC1-40 enhances mitochondrial membrane potential, increases the quantity of mitochondria, and augments the expression or activity of genes or proteins related to mitochondria, thereby enhancing mitochondrial biosynthesis to efficiently prevent, improve, or treat sarcopenia.

DETAILS OF THE PRESENT INVENTION ARE DESCRIBED IN DETAIL BELOW

The present invention provides a pharmaceutical composition for preventing or treating sarcopenia, comprising JC1-40 or a pharmaceutically acceptable salt thereof as an active ingredient.

In the present invention, JC1-40 as activator of RORα protein may be represented by Chemical Formula 1 below, may have the IUPAC name of 1-methyl-3-[(4-phenylmethoxyphenyl)methyl]thiourea, the chemical formula may be $C_{16}H_{18}N_2OS$, and the molecular weight may be 286.39, but is not limited thereto. Additionally, the method of acquiring the compound may involve chemically synthesizing it via a method disclosed in the field to which the present invention 180 pertains, or utilizing a commercially available substance.

[Chemical Formula 1]

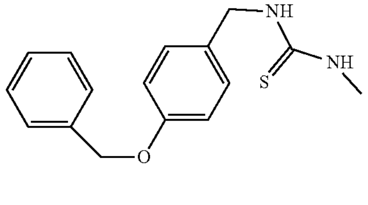

In the present invention, the JC1-40 may be included at a concentration of 1 to 100 μM, 1 to 90 μM, 1 to 80 μM, 1 to 70 μM, 1 to 60 μM, 1 to 50 μM, 2 to 100 μM, 2 to 90 μM, 2 to 80 μM, 2 to 70 μM, 2 to 60 μM, 2 to 50 μM, 3 to 100 μM, 3 to 90 μM, 3 to 80 μM, 3 to 70 μM, 3 to 60 μM, 3 to 50 μM, 4 to 100 μM, 4 to 90 μM, 4 to 80 μM, 4 to 70 μM, 4 to 60 μM, 4 to 50 μM, 5 to 100 μM, 5 to 90 μM, 5 to 80 μM, 5 to 70 μM, 5 to 60 μM, 5 to 50 μM, 10 to 50 μM, 10 to 40 μM, 10 to 30 μM, or 20 μM but is not limited thereto. Additionally, JC1-40 may satisfy at least one of the followings, but is not limited thereto: a) increasing mitochondrial membrane potential; b) increasing mitochondrial quantity; and c) increasing mitochondrial biosynthesis. Furthermore, JC1-40 may particularly satisfy at least one of the aforementioned characteristics in muscle cells, but is not limited thereto.

In the present invention, the JC1-40 may increase the expression or activity of a gene or protein selected from the group consisting of SDHA, COX5A, MCAD, PGC-1α, NRF1, NRF2α, and TFAM, but is not limited thereto. The expression or activity of the TFAM gene or protein may be dependent on RORα, but is not limited thereto.

In the present invention, "RORα (RAR-related orphan receptor alpha)" is one of the steroid hormone receptor superfamilies and is a transcription factor that regulates gene expression. In muscles, RORα promotes muscle differentiation through direct binding with p300 and MyoD. When RORα is activated, the activity of mitochondrial complex II and the formation of supercomplexes may increase, but are not limited thereto.

In the present invention, "sarcopenia" is a degenerative disease in which muscle mass and strength decrease, and, unlike muscle loss that appears in the normal aging process, refers to a disease in which muscle mass decreases abnormally rapidly. Such sarcopenia may be divided into primary sarcopenia, caused by aging, and secondary sarcopenia, caused by various causes. Causes of the secondary sarcopenia include malnutrition, decreased activity, obesity, organ failure, drugs, inflammation, malignancy, or endocrine metabolic diseases. The sarcopenia may be due to mitochondrial dysfunction, but is not limited thereto. According to an embodiment of the present invention, it may be obese sarcopenia or senile sarcopenia, and preferably may be obese sarcopenia, but is not limited thereto.

In the present invention, the mitochondrial biosynthesis activity may improve oxidative metabolism and tissue bioenergy production, and improve muscular function in sarcopenia diseases, but is not limited thereto.

The present invention may also comprise a pharmaceutically acceptable salt of the compound JC1-40 as an active ingredient. In the present invention, the term "pharmaceutically acceptable salt" comprises a salt derived from pharmaceutically acceptable inorganic acids, organic acids, or bases.

Examples of suitable acids include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, gluconic acid, naphthalene-2-sulfonic acid, benzene sulfonic acid, etc. Acid addition salts may be manufactured by conventional methods, for example, by dissolving the compound in an excess of an acid aqueous solution and precipitating this salt using a water-miscible organic solvent such as methanol, ethanol, acetone, or acetonitrile. Acid addition salts may also be prepared by heating an equimolar amount of the compound and an acid or alcohol in water and subsequently evaporating the mixture to dryness, or by aspiration-filtration of the precipitated salt.

Salts derived from suitable bases may include alkali metals such as sodium, potassium, alkaline earth metals such as magnesium, and ammonium, but are not limited thereto. Alkali metal or alkaline earth metal salts, for example, may be obtained by dissolving the compound in an excess of alkali metal hydroxide or alkaline earth metal hydroxide solution, filtering off the insoluble compound salt, and then evaporating and drying the filtrate. Here, it is pharmaceutically suitable to manufacture particularly sodium, potassium, or calcium salts as the metal salts, and the corresponding silver salts may be obtained by reacting an alkali metal or alkaline earth metal salt with a suitable silver salt (for example, silver nitrate).

The inventors of the present invention have confirmed that the compound JC1-40 exhibits excellent effects in increasing mitochondrial membrane potential and mitochondrial quantity (refer to Examples 1 and 2), have confirmed that the expression and activity of mitochondrial-related genes and proteins are notably enhanced (refer to Examples 3 and 4), and have confirmed that the expression of the mitochondrial biosynthesis regulator TFAM increases in a RORα-dependent manner, and that the effect of JC1-40 in increasing mitochondrial biosynthesis in a hyperlipidemia-induced animal model is remarkable (refer to Examples 5 and 6).

Therefore, JC1-40 or a pharmaceutically acceptable salt thereof of the present invention may be provided as a pharmaceutical composition for preventing or treating sarcopenia; or a composition for increasing mitochondrial biosynthesis.

Furthermore, the present invention provides a method for preventing or treating sarcopenia, comprising the step of administering JC1-40 or a pharmaceutically acceptable salt thereof to a subject in need thereof.

Moreover, the present invention provides a use of JC1-40 or a pharmaceutically acceptable salt thereof for preventing or treating sarcopenia.

Additionally, the present invention provides a use of JC1-40 or a pharmaceutically acceptable salt thereof for producing a drug for preventing or treating sarcopenia.

Also, the present invention provides a method for increasing mitochondrial biosynthesis, comprising the step of administering JC1-40 or a pharmaceutically acceptable salt thereof to a subject in need thereof.

In addition, the present invention provides a use of JC1-40 or a pharmaceutically acceptable salt thereof for increasing mitochondrial biosynthesis.

Furthermore, the present invention provides a use of JC1-40 or a pharmaceutically acceptable salt thereof for producing a drug to increase mitochondrial biosynthesis.

The content of the compound JC1-40 or a pharmaceutically acceptable salt thereof in the composition of the present invention may be appropriately adjusted depending on symptoms of the disease, progression of symptoms, and the condition of the patient, for example, it may be 0.0001 to 99.9 wt % or 0.001 to 50 wt % based on the total weight of the composition, but is not limited thereto. The aforementioned content ratio is based on the dry weight with the solvent removed.

The pharmaceutical composition according to the present invention may further include a suitable carrier, excipient, and diluent which are commonly used in the preparation of pharmaceutical compositions. The excipient may be, for example, one or more selected from the group consisting of a diluent, a binder, a disintegrant, a lubricant, an adsorbent, a humectant, a film-coating material, and a controlled release additive.

The pharmaceutical composition according to the present invention may be used by being formulated, according to commonly used methods, into a form such as powders, granules, sustained-release-type granules, enteric granules, liquids, eye drops, elixirs, emulsions, suspensions, spirits, troches, aromatic water, lemonades, tablets, sustained-release-type tablets, enteric tablets, sublingual tablets, hard capsules, soft capsules, sustained-release-type capsules, enteric capsules, pills, tinctures, soft extracts, dry extracts, fluid extracts, injections, capsules, perfusates, or a preparation for external use, such as plasters, lotions, pastes, sprays, inhalants, patches, sterile injectable solutions, or aerosols. The preparation for external use may have a formulation such as creams, gels, patches, sprays, ointments, plasters, lotions, liniments, pastes, or cataplasmas.

As the carrier, the excipient, and the diluent that may be included in the pharmaceutical composition according to the present invention, lactose, dextrose, sucrose, oligosaccharides, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil may be used.

For formulation, commonly used diluents or excipients such as fillers, thickeners, binders, wetting agents, disintegrants, and surfactants are used.

As additives of tablets, powders, granules, capsules, pills, and troches according to the present invention, excipients such as corn starch, potato starch, wheat starch, lactose, white sugar, glucose, fructose, D-mannitol, precipitated calcium carbonate, synthetic aluminum silicate, dibasic calcium phosphate, calcium sulfate, sodium chloride, sodium hydrogen carbonate, purified lanolin, microcrystalline cellulose, dextrin, sodium alginate, methyl cellulose, sodium carboxymethylcellulose, kaolin, urea, colloidal silica gel, hydroxypropyl starch, hydroxypropyl methylcellulose (HPMC), HPMC 1928, HPMC 2208, HPMC 2906, HPMC 2910, propylene glycol, casein, calcium lactate, and Primojel®; and binders such as gelatin, Arabic gum, ethanol, agar powder, cellulose acetate phthalate, carboxymethylcellulose, calcium carboxymethylcellulose, glucose, purified water, sodium caseinate, glycerin, stearic acid, sodium carboxymethylcellulose, sodium methylcellulose, methylcellulose, microcrystalline cellulose, dextrin, hydroxycellulose, hydroxypropyl starch, hydroxymethylcellulose, purified shellac, starch, hydroxypropyl cellulose, hydroxypropyl methylcellulose, polyvinyl alcohol, and polyvinylpyrrolidone may be used, and disintegrants such as hydroxypropyl methylcellulose, corn starch, agar powder, methylcellulose, bentonite, hydroxypropyl starch, sodium carboxymethylcellulose, sodium alginate, calcium carboxymethylcellulose, calcium citrate, sodium lauryl sulfate, silicic anhydride, 1-hydroxypropylcellulose, dextran, ion-exchange resin, polyvinyl acetate, formaldehyde-treated casein and gelatin, alginic acid, amylose, guar gum, sodium bicarbonate, polyvinylpyrrolidone, calcium phosphate, gelled starch, Arabic gum, amylopectin, pectin, sodium polyphosphate, ethyl cellulose, white sugar, magnesium aluminum silicate, a di-sorbitol solution, and light anhydrous silicic acid; and lubricants such as calcium stearate, magnesium stearate, stearic acid, hydrogenated vegetable oil, talc, lycopodium powder, kaolin, Vaseline® (petrolatum), sodium stearate, cacao butter, sodium salicylate, magnesium salicylate, polyethylene glycol (PEG) 4000, PEG 6000, liquid paraffin, hydrogenated soybean oil (Lubri wax™), aluminum stearate, zinc stearate, sodium lauryl sulfate, magnesium oxide, Macrogol, synthetic aluminum silicate, silicic anhydride, higher fatty acids, higher alcohols, silicone oil, paraffin oil, polyethylene glycol fatty acid ether, starch, sodium chloride, sodium acetate, sodium oleate, dl-leucine, and light anhydrous silicic acid may be used.

As additives of liquids according to the present invention, water, dilute hydrochloric acid, dilute sulfuric acid, sodium citrate, monostearic acid sucrose, polyoxyethylene sorbitol fatty acid esters (twin esters), polyoxyethylene monoalkyl ethers, lanolin ethers, lanolin esters, acetic acid, hydrochloric acid, ammonia water, ammonium carbonate, potassium hydroxide, sodium hydroxide, prolamine, polyvinylpyrrolidone, ethylcellulose, and sodium carboxymethylcellulose may be used.

In syrups according to the present invention, a white sugar solution, other sugars or sweeteners, and the like may be used, and as necessary, a fragrance, a colorant, a preservative, a stabilizer, a suspending agent, an emulsifier, a viscous agent, or the like may be used.

In emulsions according to the present invention, purified water may be used, and as necessary, an emulsifier, a preservative, a stabilizer, a fragrance, or the like may be used.

In suspensions according to the present invention, suspending agents such as acacia, tragacanth, methylcellulose, carboxymethylcellulose, sodium carboxymethylcellulose, microcrystalline cellulose, sodium alginate, hydroxypropyl methylcellulose (HPMC), HPMC 1828, HPMC 2906, HPMC 2910, and the like may be used, and as necessary, a surfactant, a preservative, a stabilizer, a colorant, and a fragrance may be used.

Injections according to the present invention may include: solvents such as distilled water for injection, a 0.9% sodium chloride solution, Ringer's solution, a dextrose solution, a dextrose+sodium chloride solution, PEG, lactated Ringer's solution, ethanol, propylene glycol, non-volatile oil-sesame oil, cottonseed oil, peanut oil, soybean oil, corn oil, ethyl oleate, isopropyl myristate, and benzene benzoate; cosolvents such as sodium benzoate, sodium salicylate, sodium acetate, urea, urethane, monoethylacetamide, butazolidine, propylene glycol, the TWEEN® series, amide nicotinate, hexamine, and dimethylacetamide; buffers such as weak acids and salts thereof (acetic acid and sodium acetate), weak bases and salts thereof (ammonia and ammonium acetate), organic compounds, proteins, albumin, peptone, and gums; isotonic agents such as sodium chloride; stabilizers such as sodium bisulfite ($NaHSO_3$) carbon dioxide gas, sodium metabisulfite ($Na_2S_2O_5$), sodium sulfite ($Na_2SO_3$), nitrogen gas ($N_2$), and ethylenediamine tetraacetic acid; sulfating agents such as 0.1% sodium bisulfide, sodium formaldehyde sulfoxylate, thiourea, disodium ethylenediaminetetraacetate, and acetone sodium bisulfite; a pain relief agent such as benzyl alcohol, chlorobutanol, procaine hydrochloride, glucose, and calcium gluconate; and suspending agents such as sodium CMC, sodium alginate, TWEEN® 80 (Polysorbate 80), and aluminum monostearate.

In suppositories according to the present invention, bases such as cacao butter, lanolin, WITEMSOL®, polyethylene glycol, glycerogelatin, methylcellulose, carboxymethylcellulose, a mixture of stearic acid and oleic acid, SUBANAL®, cottonseed oil, peanut oil, palm oil, cacao butter+cholesterol, lecithin, lanette wax, glycerol monostearate, TWEEN® or span, imhausen, Monolan® (propylene glycol monostearate), glycerin, Adeps solidus, buytyrum TEGO®-G, cebes Pharma 16, hexalide base 95, cotomar, HYDROKOTE® SP, S-70-XXA, S-70-XX75(S-70-XX95), HYDROKOTE® 25, HYDROKOTE® 711, idropostal, massa estrarium (A, AS, B, C, D, E, I, T), masa-MF, masupol, masupol-15, neosuppostal-N, paramount-B, supposiro (OSI, OSIX, A, B, C, D, H, L), suppository base IV types (AB, B, A, BC, BBG, E, BGF, C, D, 299), suppostal (N, Es), Wecoby (W, R, S, M, Fs), and tegester triglyceride matter (TG-95, MA, 57) may be used.

Solid preparations for oral administration include tablets, pills, powders, granules, capsules, and the like, and such solid preparations are formulated by mixing the composition with at least one excipient, e.g., starch, calcium carbonate, sucrose, lactose, gelatin, and the like. In addition to simple excipients, lubricants such as magnesium stearate and talc are also used.

Examples of liquid preparations for oral administration include suspensions, liquids for internal use, emulsions, syrups, and the like, and these liquid preparations may include, in addition to simple commonly used diluents, such as water and liquid paraffin, various types of excipients, for example, a wetting agent, a sweetener, a fragrance, a preservative, and the like. Preparations for nonoral administration include an aqueous sterile solution, a non-aqueous solvent, a suspension, an emulsion, a freeze-dried preparation, and a suppository. Non-limiting examples of the non-aqueous solvent and the suspension include propylene glycol, polyethylene glycol, a vegetable oil such as olive oil, and an injectable ester such as ethyl oleate.

The pharmaceutical composition according to the present invention is administered in a pharmaceutically effective amount. In the present invention, "the pharmaceutically effective amount" refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields.

The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

The pharmaceutical composition of the present invention may be administered to a subject via various routes. All administration methods can be predicted, and the pharmaceutical composition may be administered via, for example, oral administration, subcutaneous injection, intraperitoneal injection, intravenous injection, intramuscular injection, intrathecal (space around the spinal cord) injection, sublingual administration, administration via the buccal mucosa, intrarectal insertion, intravaginal insertion, ocular administration, intra-aural administration, intranasal administration, inhalation, spraying via the mouth or nose, transdermal administration, percutaneous administration, or the like.

The pharmaceutical composition of the present invention is determined depending on the type of a drug, which is an active ingredient, along with various related factors such as a disease to be treated, administration route, the age, gender, and body weight of a patient, and the severity of diseases.

As used herein, the "subject" refers to a subject in need of treatment of a disease, and more specifically, refers to a mammal such as a human or a non-human primate, a mouse, a rat, a dog, a cat, a horse, and a cow, but the present invention is not limited thereto.

As used herein, the "administration" refers to providing a subject with a predetermined composition of the present invention by using an arbitrary appropriate method.

The term "prevention" as used herein means all actions that inhibit or delay the onset of a target disease. The term "treatment" as used herein means all actions that alleviate or beneficially change a target disease and abnormal metabolic symptoms caused thereby via administration of the pharmaceutical composition according to the present invention. The term "improvement" as used herein means all actions that reduce the degree of parameters related to a target disease, e.g., symptoms via administration of the composition according to the present invention.

Furthermore, the present invention provides a food composition for preventing or improving sarcopenia, comprising JC1-40 or a food acceptable salt thereof as an active ingredient. The food composition comprises a health functional food composition.

When using JC1-40 or a food acceptable salt thereof of the present invention as a food additive, the JC1-40 or the food acceptable salt thereof may be directly added or may be used together with other food or food ingredients, and may be used appropriately according to conventional methods. The mixed amount of the active ingredient may be suitably determined depending on the purpose of use (prevention, health, or therapeutic treatment). Generally, when manufacturing food or beverages, JC1-40 or a food acceptable salt thereof of the present invention may be added in an amount of 15 wt % or less, or 10 wt % or less based on the raw material. However, for long-term intake aimed at health and sanitation or health regulation, the amount may be below the aforementioned range and since there are no issues in terms of safety, the active ingredient may be used in amounts above the aforementioned range.

The type of food is not particularly limited. Examples of food to which the material may be added include meats, sausage, bread, chocolate, candies, snacks, confectioneries, pizza, instant noodles, other noodles, gums, dairy products including ice creams, various soups, beverages, tea, drinks, alcoholic beverages, vitamin complexes, and the like, and include all health functional foods in a typical sense.

The health beverage composition according to the present invention may contain various flavors or natural carbohydrates, and the like as additional ingredients as in a typical beverage. The aforementioned natural carbohydrates may be monosaccharides such as glucose and fructose, disaccharides such as maltose and sucrose, polysaccharides such as dextrin and cyclodextrin, and sugar alcohols such as xylitol, sorbitol, and erythritol. As a sweetener, it is possible to use a natural sweetener such as thaumatin and *stevia* extract, a synthetic sweetener such as saccharin and aspartame, and the like. The proportion of the natural carbohydrates is generally about 0.01 to 0.20 g, or about 0.04 to 0.10 g per 100 ml of the composition of the present invention.

In addition to the aforementioned ingredients, the composition of the present invention may contain various nutrients, vitamins, electrolytes, flavors, colorants, pectic acids and salts thereof, alginic acid and salts thereof, organic acids, protective colloid thickeners, pH adjusters, stabilizers, preservatives, glycerin, alcohols, carbonating agents used in carbonated drinks, and the like. In addition, the composition of the present invention may contain flesh for preparing natural fruit juice, fruit juice drinks, and vegetable drinks. These ingredients may be used either alone or in combinations thereof. The proportion of these additives is not significantly important, but is generally selected within a range of 0.01 to 0.20 part by weight per 100 parts by weight of the composition of the present invention.

Moreover, the present invention provides a cosmetic composition for improving muscular function, comprising JC1-40 or a cosmetically acceptable salt thereof as an active ingredient.

Additionally, the present invention provides a method for improving muscular function, comprising a step of administering JC1-40 or a salt thereof to a subject in need thereof.

Furthermore, the present invention provides a use of JC1-40 or a salt thereof for improving muscular function.

Also, the present invention provides a use of JC1-40 or a cosmetically acceptable salt thereof for producing a cosmetic utilized for improving muscular function.

In the present invention, "improving muscular function" refers to ameliorating muscle mass reduction occurring due to aging, obesity, and the like. The muscular function may be proportional to muscle mass, but is not limited thereto.

A formulation for the cosmetic composition according to the present invention may include a skin lotion, a skin softener, a skin toner, an astringent, a lotion, a milk lotion, a moisturizing lotion, a nourishing lotion, a massage cream, a nourishing cream, a mist, a moisturizing cream, a hand cream, a hand lotion, a foundation, an essence, a nourishing essence, a pack, soap, a cleansing foam, a cleansing lotion, a cleansing cream, a cleansing oil, a cleansing balm, a body lotion or a body cleanser.

A cosmetic composition of the present invention may further include a composition selected from the group consisting of water-soluble vitamins, oil-soluble vitamins, polymer peptides, polymeric polysaccharides, and sphingolipids.

The water-soluble vitamin may be any substance that is blendable with cosmetics, but examples thereof include vitamin B1, vitamin B2, vitamin B6, pyridoxine, pyridoxine hydrochloride, vitamin B12, pantothenic acid, nicotinic acid, nicotinic acid amide, folic acid, vitamin C, vitamin H, and the like, and salts thereof (thiamine hydrochloride, sodium ascorbate, and the like) or derivatives thereof (sodium ascorbic acid-2-phosphate, magnesium ascorbic acid-2-phosphate, and the like) are also included in water-soluble vitamins that may be used in the present invention. These water-soluble vitamins may be obtained by a conventional method such as microbial transformation, purification from a microbial culture, an enzyme method, or a chemical synthesis method.

The oil-soluble vitamins may be any substance that is blendable with cosmetics, but examples thereof include vitamin A, carotene, vitamin D2, vitamin D3, vitamin E (dl-α-tocopherol, d-α-tocopherol), or the like, and derivatives thereof (e.g., ascorbyl palmitate, ascorbyl stearate, ascorbyl dipalmitate, dl-α-tocopherol acetate, dl-α-tocopherol nicotinate, vitamin E, DL-pantothenyl alcohol, D-pantothenyl alcohol, pantothenyl ethylether) may also be included in the oil-soluble vitamins used in the present invention. These oil-soluble vitamins may be obtained by a conventional method such as microbial transformation, purification from a microbial culture, or enzymatic or chemical synthesis.

The polymer peptides may be any substance that is blendable with cosmetics, but examples thereof may include collagen, hydrolyzed collagen, gelatin, elastin, hydrolyzed elastin, and keratin. The polymer peptides may be purified and obtained by any conventional method such as purification from a microbial culture, an enzyme method, or a chemical synthesis method, or may generally be used by being purified from natural substances such as the dermis of a pig, a cow, or the like and silk fiber of silkworms.

The polymeric polysaccharides may be any substance that is blendable with cosmetics, and examples thereof may include hydroxyethyl cellulose, xanthan gum, sodium hyaluronate, and chondroitin sulfate or salts thereof (sodium salts). For example, chondroitin sulfate or salts thereof may generally be purified from mammals or fish and used.

The sphingolipids may be any substance that is blendable with cosmetics, and examples thereof may include ceramide, phytosphingosine, and sphingoglycolipid. The sphingolipids may be purified, by a conventional method, from mammals, fish, shellfish, yeast, or plants, or may be obtained by a chemical synthesis method.

The cosmetic composition of the present invention may include, as necessary, other ingredients mixed in conventional cosmetics along with the above essential ingredients.

Examples of additional ingredients to be mixed may include lipid components, a humectant, an emollient, a surfactant, organic and inorganic pigments, organic powder, a UV absorbent, a preservative, a sanitizer, an antioxidant, a plant extract, a pH adjuster, alcohol, pigments, flavors, a blood circulation promoter, a cooling agent, an anti-diaphoretic, and purified water.

The lipid components may include, for example, ester lipids, hydrocarbon lipids, silicone lipids, fluorine lipids, animal fats, vegetable oil, or the like.

The ester lipids may include, for example, glyceryl tri 2-ethylhexanoate, cetyl 2-ethylhexanoate, isopropyl myristate, butyl myristate, isopropyl palmitate, ethyl stearate, octyl palmitate, isocetyl isostearate, butyl stearate, ethyl linolate, isopropyl linolate, ethyl oleate, isocetyl myristate, isostearyl myristate, isostearyl palmitate, octyldodecyl myristate, isocetyl isostearate, diethyl sebacate, diisopropyl adipate, isoalkyl neopentanate, tri(capryl, capric acid)glyceryl, trimethylolpropane tri 2-ethylhexanoate, trimethylolpropane triisostearate, pentaerythritol tetra 2-ethylhexanoate, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl palmitate, octyl stearate, isocetyl stearate, isodecyl oleate, octyldodecyl oleate, octyldodecyl linolate, isopropyl isostearate, cetostearyl 2-ethylhexanoate, stearyl 2-ethylhexanoate, hexyl isostearate, ethyleneglycol dioctanoate, ethyleneglycol dioleate, propyleneglycol dicaprinate, propyleneglycol di(caprylate, caprinate), propyleneglycol dicaprylate, neopentylglycol dicaprinate, neopentylglycol dioctanoate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isocetyl isostearate, isostearyl isostearate, octyldecyl isostearate, polyglycerin ester oleate, polyglycerin ester isostearate, triisocetyl citrate, triisoalkyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, di 2-ethylhexyl succinate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoyl hydroxystearate, stearoyl 12-stearoyl hydroxystearate, isostearyl 12-stearoyl hydroxystearate, and the like.

The hydrocarbon lipids may include, for example, squalene, liquid paraffin, alpha-olefin oligomers, isoparaffin, ceresine, paraffin, liquid isoparaffin, polybutene, microcrystalline wax, Vaseline® (petrolatum), and the like.

The silicone lipids may include, for example, polymethyl silicon, methylphenyl silicon, methyl cyclopolysiloxane, octamethyl polysiloxane, decamethyl polysiloxane, dodecamethyl cyclosiloxane, dimethylsiloxane/methylcetyloxysiloxane copolymers, dimethylsiloxane/methylstearoxysiloxane copolymers, alkyl-modified silicon oil, amino-modified silicon oil, and the like.

The fluorine lipids may include perfluoropolyether and the like.

The animal or vegetable oil may include avocado oil, almond oil, olive oil, sesame oil, rice bran oil, safflower oil, soybean oil, corn oil, rape flower oil, apricot kernel oil, palm kernel oil, palm oil, castor oil, sunflower oil, grape seed oil, cotton seed oil, coconut oil, tallow nut oil, wheat germ oil, rice germ oil, Shea butter, evening primrose oil, macadamia nut oil, meadow foam seed oil, yolk oil, beef tallow, hemp seed oil, mink oil, orange roughy oil, jojoba oil, candelilla wax, carnauba wax, liquid lanolin, dehydrated castor oil, and the like.

The humectant may include water-soluble low molecular humectants, oil-soluble molecular humectants, water-soluble polymers, oil-soluble polymers, and the like.

The water-soluble low molecular humectants may include serine, glutamine, sorbitol, mannitol, pyrrolidone-sodium carboxylate, glycerin, propylene glycol, 1,3-butylene glycol, ethylene glycol, polyethylene glycol B (degree of polymerization: n=2 or higher), polypropylene glycol (degree of polymerization: n=2 or higher), polyglycerin B (degree of polymerization: n=2 or higher), lactic acid, lactates, and the like.

The oil-soluble low molecular humectants may include cholesterol, cholesterol ester, and the like.

The water-soluble polymers may include carboxyvinyl polymers, polyasparaginic acid salts, tragacanth, xanthan gum, methyl cellulose, hydroxymethyl cellulose, hydroxylethyl cellulose, hydroxypropyl cellulose, carboxymethyl cellulose, water-soluble chitin, chitosan, dextrin, and the like.

The oil-soluble polymers may include, for example, polyvinyl pyrrolidone/eicosen copolymers, polyvinyl pyrrolidone/hexadecene copolymers, nitrocellulose, dextrin fatty acid ester, silicone polymers, and the like.

The emollients may include, for example, long chain cholesterylester acyl glutamate, cholesteryl hydroxystearate, 12-hydroxystearic acid, stearic acid, rosin acid, lanolin fatty acid cholesteryl ester, and the like.

The surfactants may include, for example, non-ionic surfactants, anionic surfactants, cationic surfactants, amphoteric surfactants, and the like.

The non-ionic surfactants may include self-emulsion type glycerin monostearate, propyleneglycol fatty acid ester, glycerin fatty acid ester, polyglycerin fatty acid ester, sorbitan fatty acid ester, polyoxyethylene (POE) sorbitan fatty acid ester, POE sorbit fatty acid ester, POE glycerin fatty acid ester, POE alkylethers, POE fatty acid ester, POE dehydrated castor oil, POE castor oil, polyoxyethylene/polyoxypropylene (POE/POP) copolymers, POE/POP alkylethers, polyether-modified silicone, alkanolamide laurate, alkylamine oxide, hydrated soy phospholipids, and the like.

The anionic surfactants may include fatty acid soap, α-acylsulfonate, alkyl sulfonates, alkylallyl sulfonates, alkylnaphthalene sulfonates, alkyl sulfates, POE alkylether sulfates, alkylamide sulfates, alkyl phosphates, POE alkyl phosphates, alkylamide phosphates, alkyloyl alkyltaurin salts, N-acylamino acid salts, POE alkylether carboxylates, alkyl sulfosuccinates, sodium alkyl sulfoacetates, acylated hydrolyzed collagen peptide salts, perfluoroalkyl ester phosphates, and the like.

The cationic surfactants may include, for example, alkyltrimethylammonium chloride, stearyltrimethylammonium chloride, steraryltrimethylammonium bromide, cetostearyl trimethylammonium chloride, distearyl dimethylammonium chloride, stearylaryl dimethylbenzylammonium chloride, behenyltrimethylammonium bromide, benzalkonium chloride, diethylaminoethylamide stearate, dimethylaminopropylamide stearate, quaternary ammonium salts of lanolin derivatives, and the like.

The amphoteric surfactants may include carboxybetaine, amidebetaine, sulfobetaine, hydroxysulfobetaine, amidesulfobetaine, phosphobetaine, aminocarboxylate, imidazoline derivatives, amideamine-based amphoteric surfactants, and the like.

The organic and inorganic pigments may include: inorganic pigments such as silicic acid, anhydrous silicic acid, magnesium silicate, talc, sericite, mica, kaolin, bengala, clay, bentonite, titanium dioxide-coated mica, bismuth oxychloride, zirconium oxide, magnesium oxide, zinc oxide, titanium oxide, aluminum oxide, calcium sulfate, barium sulfate, magnesium sulfate, calcium carbonate, magnesium carbonate, iron oxide, ultramarine, chromium oxide, chromium hydroxide, calamine, and combinations thereof; organic pigments such as polyamide, polyester, polypropylene, polystyrene, polyurethane, vinyl resin, urea resin, phenol resin, fluorine resin, silicon resin, acryl resin, melamine resin, epoxy resin, polycarbonate resin, divinyl benzene/styrene copolymers, silk powder, cellulose, CI pigment yellow, and CI pigment orange; and composite pigments of inorganic and organic pigments.

The organic powder may include: metallic soap such as calcium stearate; metal salts of alkyl phosphoric acid such as zinc sodium cetylate, zinc laurylate, and calcium laurylate; polymetallic salts of acylamino acid such as calcium N-lauroyl-beta-alanine, zinc N-lauroyl-beta-alanine, and calcium N-lauroylglycine; polymetallic salts of amide sulfonates such as calcium N-lauroyl-taurine and calcium N-palmitoyl-taurine; N-acyl alkaline amino acids such as N-epsilon-lauroyl-L-lysine, N-epsilon-palmitoyl lysine, N-α-palmitoylol nitin, N-α-lauroyl arginine, and N-α-dehydrated tallow fatty acid acyl arginine; N-acyl polypeptides such as N-lauroyl glycylglycine; α-amino fatty acids such as α-aminocaprylic acid and α-aminolauric acid; polyethylene; polypropylene; nylon; polymethylmethacrylate; polystyrene; divinylbenzene/styrene copolymers; ethylene tetrafluoride; and the like.

The UV absorbents may include para-aminobenzoic acid, ethyl para-aminobenzoate, amyl para-aminobenzoate, octyl para-aminobenzoate, ethyleneglycol salicylate, phenyl salicylate, octyl salcylate, benzyl salicylate, butylphenyl salicylate, homomentyl salicylate, benzyl cinnamate, para-methoxycinnamic acid-2-ethoxylethyl, octyl paramethoxycinnamate, mono-2-ethylhexaneglyceryl diparamethoxycinnamate, isopropyl paramethoxycinnamate, diisopropyl/diisopropyl cinnamic acid ester mixtures, urocanic acid, ethyl urocanate, hydroxymethoxybenzophenone, hydroxymethoxybenzophenone sulfonic acid and salts thereof, dihydroxymethoxybenzophenone, sodium dihydroxymethoxybenzophenone disulfonate, dihydroxybenzophenone, tetrahydroxybenzophenone, 4-tert-butyl-4'-methoxydibenzoylmethane, 2,4,6-trianilino-p-(carbo-2'-ethylhexyl-1'-oxy)-1,3,5-triazine, 2-(2-hydroxy-5-methylphenyl)benzotriazole, and the like.

The sanitizers may include hinokitiol, trichloric acid, trichlorohydroxydiphenylether, chlorohexidine gluconate, phenoxyethanol, resorcine, isopropylmethylphenol, azulene, salicylic acid, zinc pyrithione, benzalkonium chloride, light sensitive element No. 301, sodium mononitroguaiacol, undecylenic acid, and the like.

The antioxidants may include butylhydroxyanisole, propyl gallate, elisorbic acid, and the like.

The pH adjusters may include citric acid, sodium citrate, malic acid, sodium malate, fumaric acid, sodium fumarate, succinic acid, sodium succinate, sodium hydroxide, sodium monohydrophosphate, and the like.

The alcohols may include higher alcohols such as cetyl alcohol.

In addition, additional ingredients to be mixed are not limited to the above examples, and any one of the above ingredients may be mixed within a range that does not adversely affect the objectives and effects of the present invention, but may range from 0.01 wt % to 5 wt % or 0.01 wt % to 3 wt % with respect to the total weight of the composition.

For lotion, paste, cream, or gel preparations of the present invention, as a carrier ingredient, animal fiber, vegetable fiber, wax, paraffin, starch, tragacanth, a cellulose derivative, polyethylene glycol, silicon, bentonite, silica, talc, zinc oxide, or the like may be used.

For powder or spray preparations of the present invention, lactose, talc, silica, aluminum hydroxide, calcium silicate, or polyamide powder may be used as a carrier ingredient. In particular, in the case of spray preparations, the composition may further include a propellant such as chlorofluorohydrocarbon, propane/butane, or dimethyl ether.

For solution or emulsion preparations of the present invention, a solvent, a solubilizing agent, or an emulsifying agent may be used as a carrier ingredient, and the carrier ingredient may be, for example, water, ethanol, isopropanol, ethyl carbonate, ethyl acetate, benzyl alcohol, benzyl benzoate, propylene glycol, 1,3-butyl glycol oil, a glycerol aliphatic ester, polyethylene glycol, or a sorbitan fatty acid ester.

For suspension preparations of the present invention, as a carrier ingredient, a liquid diluent such as water, ethanol, or propylene glycol, a suspending agent such as ethoxylated isostearyl alcohol, polyoxyethylene sorbitol ester, or polyoxyethylene sorbitan ester, micro-crystalline cellulose, aluminum methahydroxide, bentonite, agar, tragacanth, or the like may be used.

For surfactant-containing cleansing preparations of the present invention, as a carrier ingredient, an aliphatic alcohol sulfate, an aliphatic alcohol ether sulfate, a sulfosuccinate monoester, isethionate, imidazolinium derivatives, methyltaurate, sarcosinate, fatty acid amide ether sulfate, alkylamidobetaine, an aliphatic alcohol, a fatty acid glyceride, a fatty acid diethanol amide, vegetable oil, a lanolin derivative, an ethoxylated glycerol fatty acid ester, or the like may be used.

Hereinafter, preferable examples are presented to aid in the understanding of the present invention. However, these examples are provided merely for easier understanding of the present invention, and the content of the present invention is not limited by these examples.

EXAMPLE

Example 1. Verification of the Effect of JC1-40 on Increasing Mitochondrial Membrane Potential in Muscle Cells C2C12 cells ($2\times10^5$ cells/well) were seeded in a 12-well culture plate and cultivated in DMEM (Dulbecco's modified Eagle's medium) medium containing 10% FBS (fetal bovine serum). The C2C12 cells were maintained at 37° C. in a humidified incubator with 5% $CO_2$ and 95% air. After 48 hours of cultivation, the medium was changed to DMEM (Dulbecco's modified Eagle's medium) differentiation medium containing 2% horse serum, and the cells were treated with JC1-40 (20 μM) and solvent (control group). 48 hours after changing the differentiation medium, the mitochondria of the C2C12 cells were stained with Tetramethylrhodamine, Methyl Ester, and Perchlorate (TMRM) 600 nM. After 20 minutes, the medium was replaced with new medium containing TMRM 150 nM, and red fluorescence was observed after 10 minutes. The results are shown in FIG.

As shown in FIG. 1, it was confirmed that red fluorescence increased in C2C12 myotubes treated with JC1-40. This implies that the mitochondrial membrane potential was increased by JC1-40.

Example 2. Verification of the Effect of JC1-40 on Increasing Mitochondrial Quantity HeLa cells ($4\times10^4$ cells/well) were seeded in a 12-well culture plate and cultivated overnight in DMEM (Dulbecco's modified Eagle's medium) medium containing 10% FBS (fetal bovine serum). The HeLa cells were maintained at 37° C. in a humidified incubator with 5% $CO_2$ and 95% air. After 24 hours of cultivation, the medium was replaced and JC1-40 (5 μM, 50 μM), and solvent (control group) were treated for 24 hours. Subsequently, the cells were stained with MitoTracker™ Green 200 nM for 30 minutes at 37° C., fixed with 4% formaldehyde, and green fluorescence was observed with a confocal microscope. The results are shown in FIG. 2.

Figure 2:
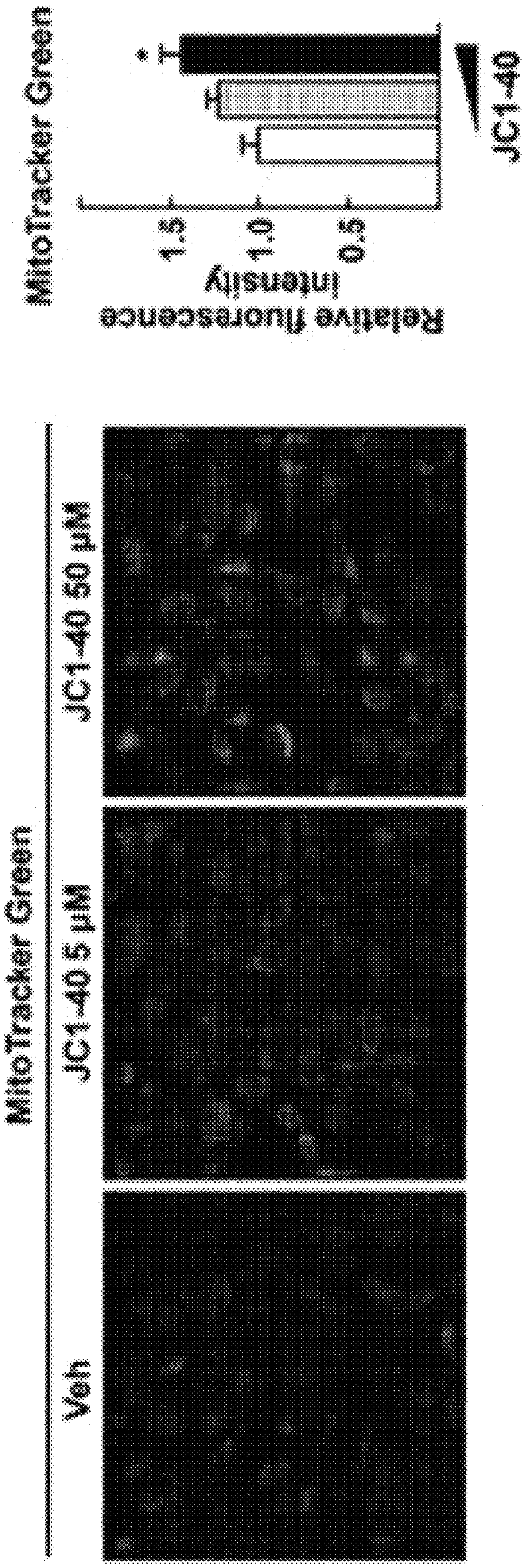
FIG. 2 shows the effect of JC1-40 on the quantity of mitochondria in HeLa cells.

As shown in FIG. 2, it was observed that green fluorescence increased in a concentration-dependent manner in HeLa cells with JC1-40. This indicates that the quantity of mitochondria was increased by JC1-40.

Figure 3:
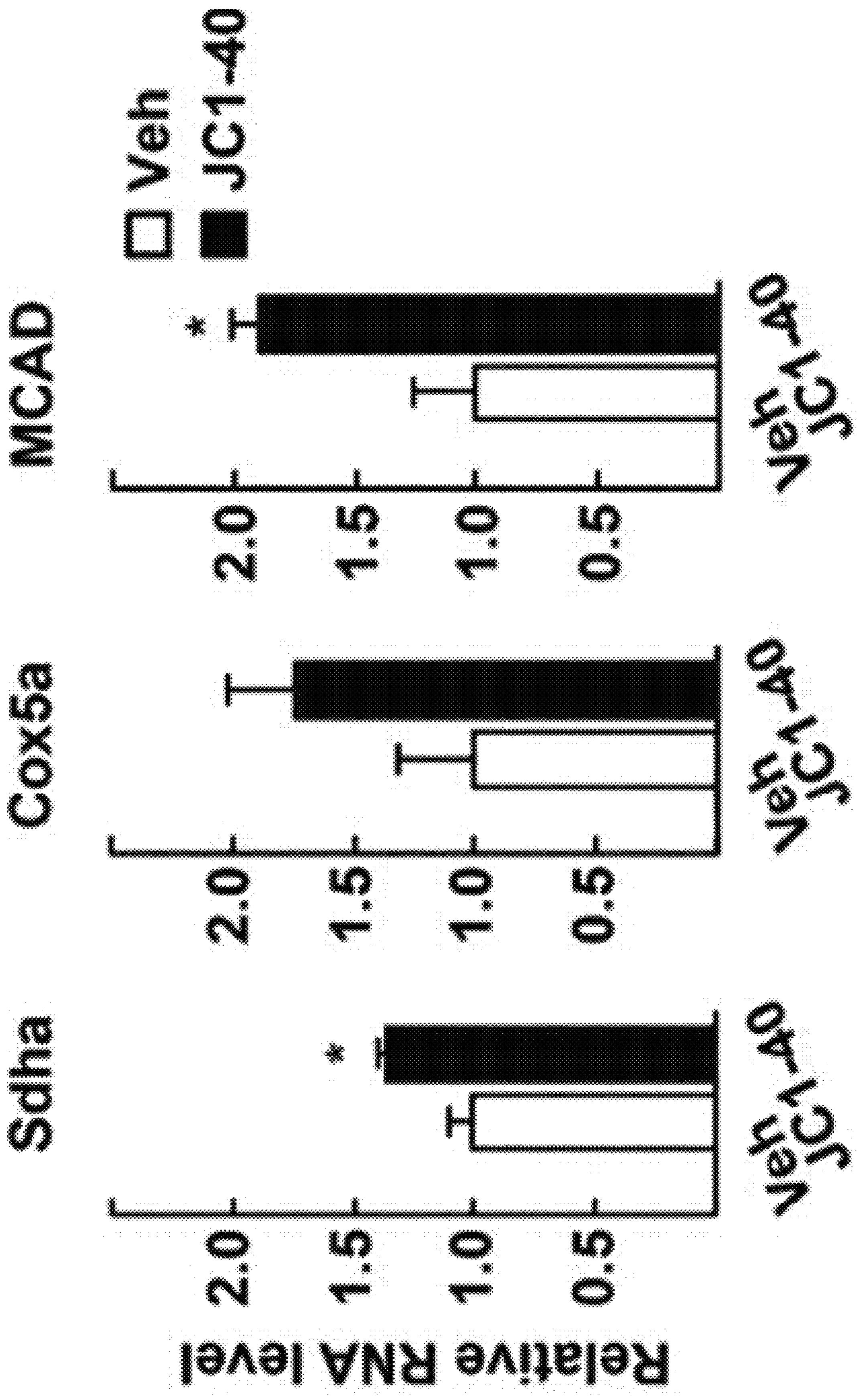
FIG. 3 shows the effect of JC1-40 on the mRNA expression of SDHA, COX5A, and MCAD in C2C12 cells.

Example 3. Verification of the Effect of JC1-40 on Increasing mRNA Expression of Mitochondrial Constituent Genes in Muscle Cells C2C12 cells ($8\times10^5$ cells/dish) were seeded in a 60 mm dish and cultured in DMEM (Dulbecco's modified Eagle's medium) medium containing 10% FBS (fetal bovine serum). C2C12 cells were maintained at 37° C. in a humidified incubator with 5% $CO_2$ and 95% air. After 48 hours of cultivation, the medium was changed to DMEM differentiation medium containing 2% horse serum, and the cells were treated with JC1-40 (20 μM) and solvent (control group). After 48 hours from the replacement of the differentiation medium, RNA was extracted. For extraction, the cells were dissolved with easy-BLUE™ (Intron, Korea), and isopropanol fractionation and ethanol precipitation were utilized. cDNA was synthesized from each RNA sample, and oligomers amplifying the cDNA of specific genes were utilized, monitoring the expression of R-actin as a control group. More specifically, an mRNA-M-MLV mixture was prepared using M-MLV reverse transcriptase (Invitrogen), and reverse transcription polymerase chain reaction was conducted using a thermal cycler. Subsequently, real-time polymerase chain reaction was performed using the ABI StepOnePlus Real-Time PCR system (Applied Biosystems). The results are shown in FIG. 3. Additionally, the primer sequences used in the experiment are presented in Table 1.

TABLE 1

| Marker | Sequence | SEQ ID NO |
|---|---|---|
| SDHA | F: GAAAGGCGGGCAGGCTCATC | 1 |
| | R: CACCACGGCACTCCCCATTTT | 2 |
| COX5A | F: TTGATGCCTGGGAATTGCGTAAAG | 3 |
| | R: AACAACCTCCAAGATGCGAACAG | 4 |
| MCAD | F: GATCGCAATGGGTGCTTTTGATAGAA | 5 |
| | R: AGCTGATTGGCAATGTCTCCAGCAAA | 6 |

As shown in FIG. 3, upon treatment with JC1-40, the mRNA expression of SDHA (Succinate dehydrogenase complex, subunit a) and COX5A (Cytochrome c oxidase subunit 5a), which are mitochondrial components, increased, as did the mRNA expression of MCAD (Medium-chain acyl-coenzyme A dehydrogenase), an enzyme associated with mitochondrial fatty acid β-oxidation.

Figure 4A:
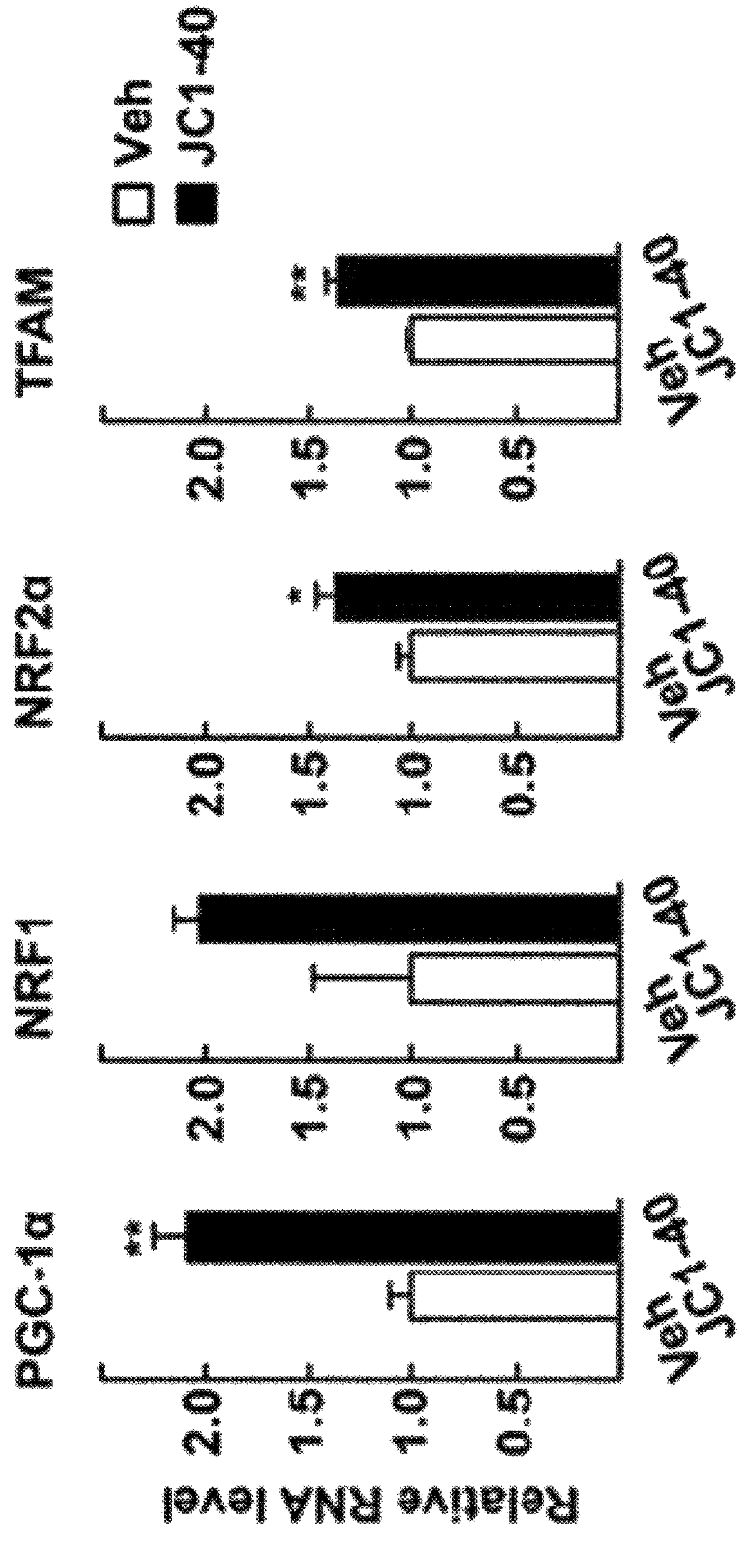
FIG. 4A shows the effect of JC1-40 on the mRNA expression of PGC-1α, NRF1, NRF2u, and TFAM in C2C12 cells.

Example 4. Verification of the Effect of JC1-40 on Increasing mRNA and Protein Expression of Mitochondrial Biosynthesis Regulatory Factor, and Promoter Activity Enhancement C2C12 cells ($8\times10^5$ cells/dish) were seeded in a 60 mm dish and cultured in DMEM (Dulbecco's modified Eagle's medium) containing 10% FBS (fetal bovine serum). The C2C12 cells were maintained at 37° C. in a humidified incubator with 5% $CO_2$ and 95% air. After 48 hours of cultivation, the medium was changed to DMEM differentiation medium containing 2% horse serum, and treated with JC1-40 (20 μM) and solvent (control group). 48 hours after changing to the differentiation medium, RNA was extracted. The RNA extraction method is as described in Example 3. The results of the mRNA expression of mitochondrial biosynthesis regulators PGC-1α (Peroxisome proliferator-activated receptor gamma coactivator 1-alpha), NRF-1 (Nuclear Respiratory Factor 1), NRF-2α (Nuclear Respiratory Factor alpha), and TFAM (Mitochondrial transcription factor A) induced by JC1-40 are shown in FIG. 4A. Additionally, the primer sequences used in the experiment are shown in Table 2 below.

TABLE 2

| Marker | Sequence | SEQ ID NO |
|---|---|---|
| PGC-1α | F: CCCTGCCATTGTTAAGACC | 7 |
| | R: TGCTGCTGTTCCTGTTTTC | 8 |
| NRF-1 | F: CCCCCGAGGACACTTCTTATGATG | 9 |
| | R: GGCCGTTTCCGTTTCTTCCCTGTT | 10 |
| NRF-2α | F: CAAGAGCAACAGATGAATGAG | 11 |
| | R: ACTTTAATCGTAGTCGGTGTAG | 12 |

TABLE 2-continued

| Marker | Sequence | SEQ ID NO |
|---|---|---|
| TFAM | F: GGAATGTGGAGCGTGCTAAAA | 13 |
| | R: ACAAGACTGATAGACGAGGGG | 14 |

Figure 4B:
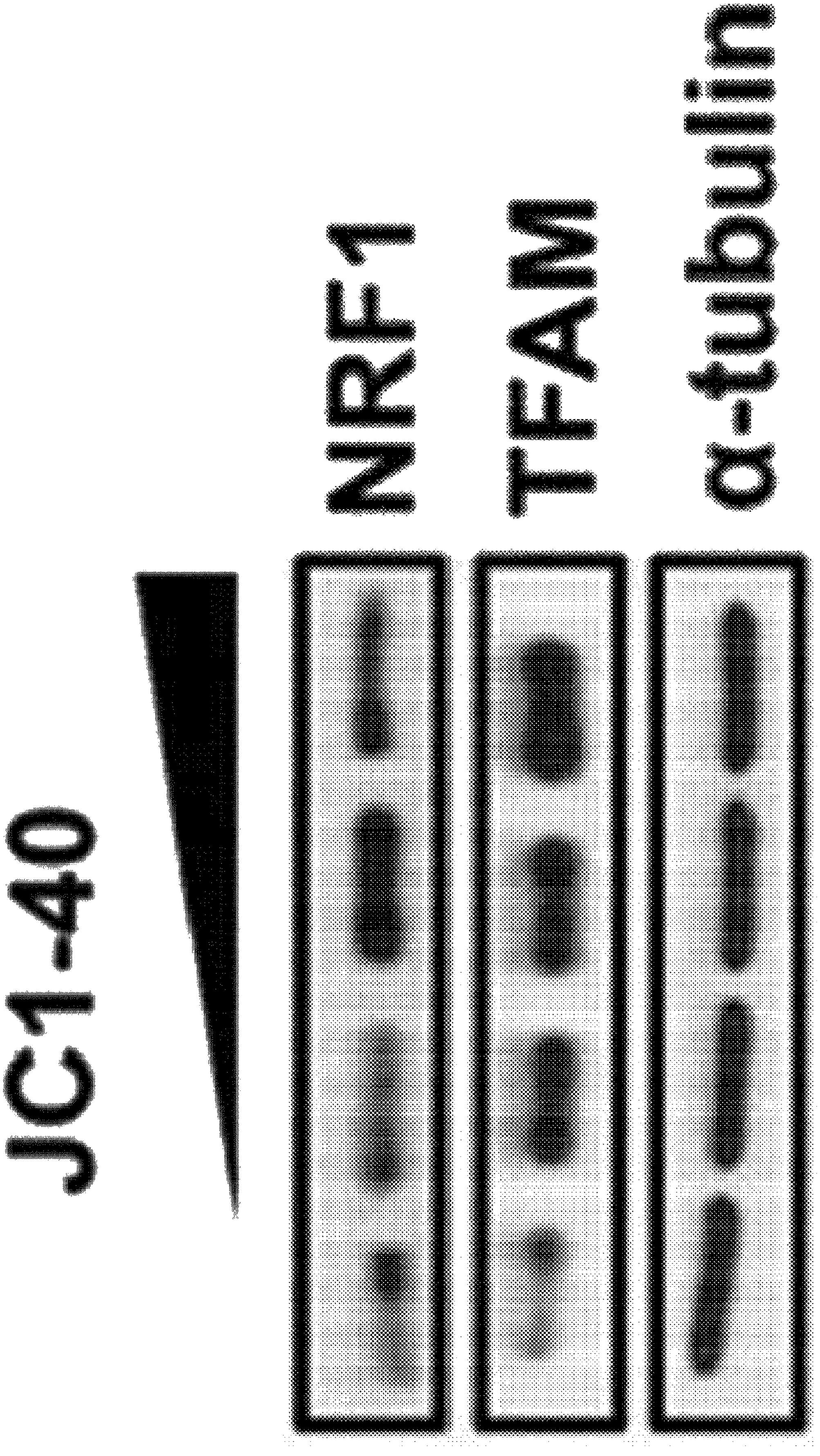
FIG. 4B shows the effect of JC1-40 on expression of NRF1 and TFAM proteins in C2C12 cells.

Using a method identical to the above, after treating C2C12 cells with the compound JC1-40, the expression of the mitochondrial biosynthesis regulators, NRF1 and TFAM proteins, was analyzed by Western blotting. Specific antibodies for NRF1 (Santa Cruz Biotechnology), TFAM (Santa Cruz Biotechnology), and α-tubulin (Millipore) were also used. The protein expression results of the mitochondrial biosynthesis regulators induced by JC1-40 are shown in FIG. 4B.

Figure 4C:
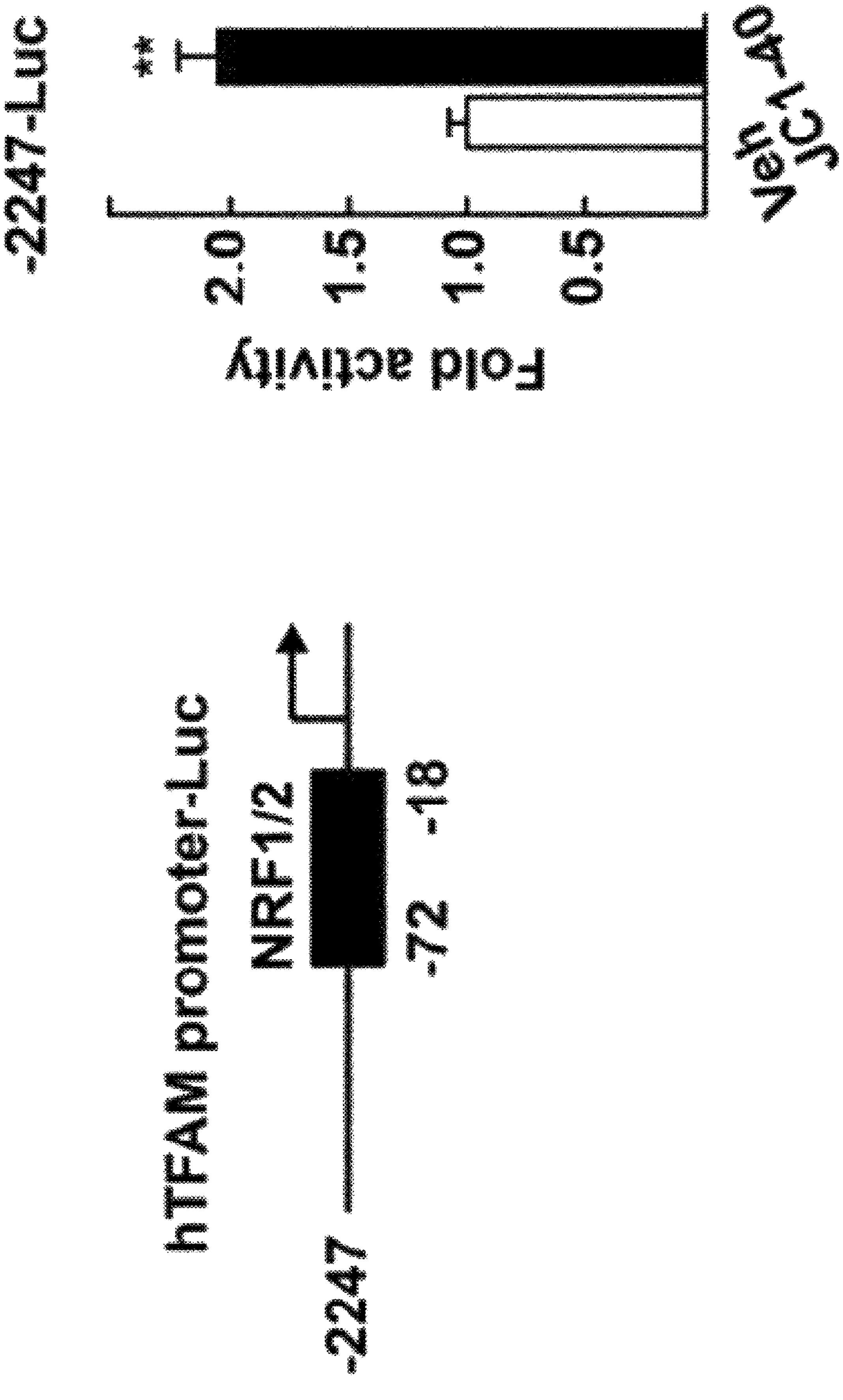
FIG. 4C shows the effect of JC1-40 on the transcriptional activity of the TFAM promoter in C2C12 cells.

C2C12 cells ($1\times10^5$ cells/well) were seeded in a 12-well culture plate and cultured overnight in DMEM containing 10% FBS. The C2C12 cells were maintained at 37° C. in a humidified incubator with 5% $CO_2$ and 95% air. After 24 hours of cultivation, human TFAM-Luc reporter (100 ng) was transfected into C2C12 cells using PolyFect™ (QIAGEN). After 24 hours post-transfection, the medium was changed to DMEM differentiation medium containing 2% horse serum, and treated with JC1-40 (20 μM) and solvent (control group). 24 hours later, cell lysates were obtained and luciferase activity was analyzed and determined using an analytical luminescence luminometer. Luciferase activity was normalized to $-gal activity for transfection efficiency, and the results are shown in FIG. 4C.

As shown in FIG. 4A, upon treatment with JC1-40, the mRNA expression of mitochondrial biosynthesis regulatory factors PGC-1α, NRF-1, NRF-2, and TFAM increased. Additionally, as shown in FIG. 4B, protein expression of NRF-1 and TFAM increased due to JC1-40. Furthermore, as shown in FIG. 4C, the increase in mRNA and protein expression of TFAM by JC1-40 was confirmed to be due to the transcriptional activity of the TFAM promoter.

Example 5. Verification of RORα-dependent Effect of JC1-40 on Increasing Mitochondrial Biosynthesis Regulator TFAM Expression C2C12 cells ($8\times10^5$ cells/dish) were seeded in a 60 mm dish and cultured overnight in DMEM (Dulbecco's modified Eagle's medium) containing 10% FBS (fetal bovine serum). The C2C12 cells were maintained at 37° C. in a humidified incubator with 5% $CO_2$ and 95% air. After 24 hours of cultivation, si-RORα (250 pmoles) and si-GL3 (control group) were transfected into C2C12 cells using Lipofectamine® 2000 (Thermo Fisher Scientific). After 24 hours post-transfection, the medium was switched to DMEM differentiation medium containing 2% horse serum, and treated with JC1-40 (20 μM) for 48 hours. The methods for RNA and protein extraction were as previously mentioned. The results of the RORα dependency of the increase in TFAM expression by JC1-40 are shown in FIG. 5.

Figure 5:
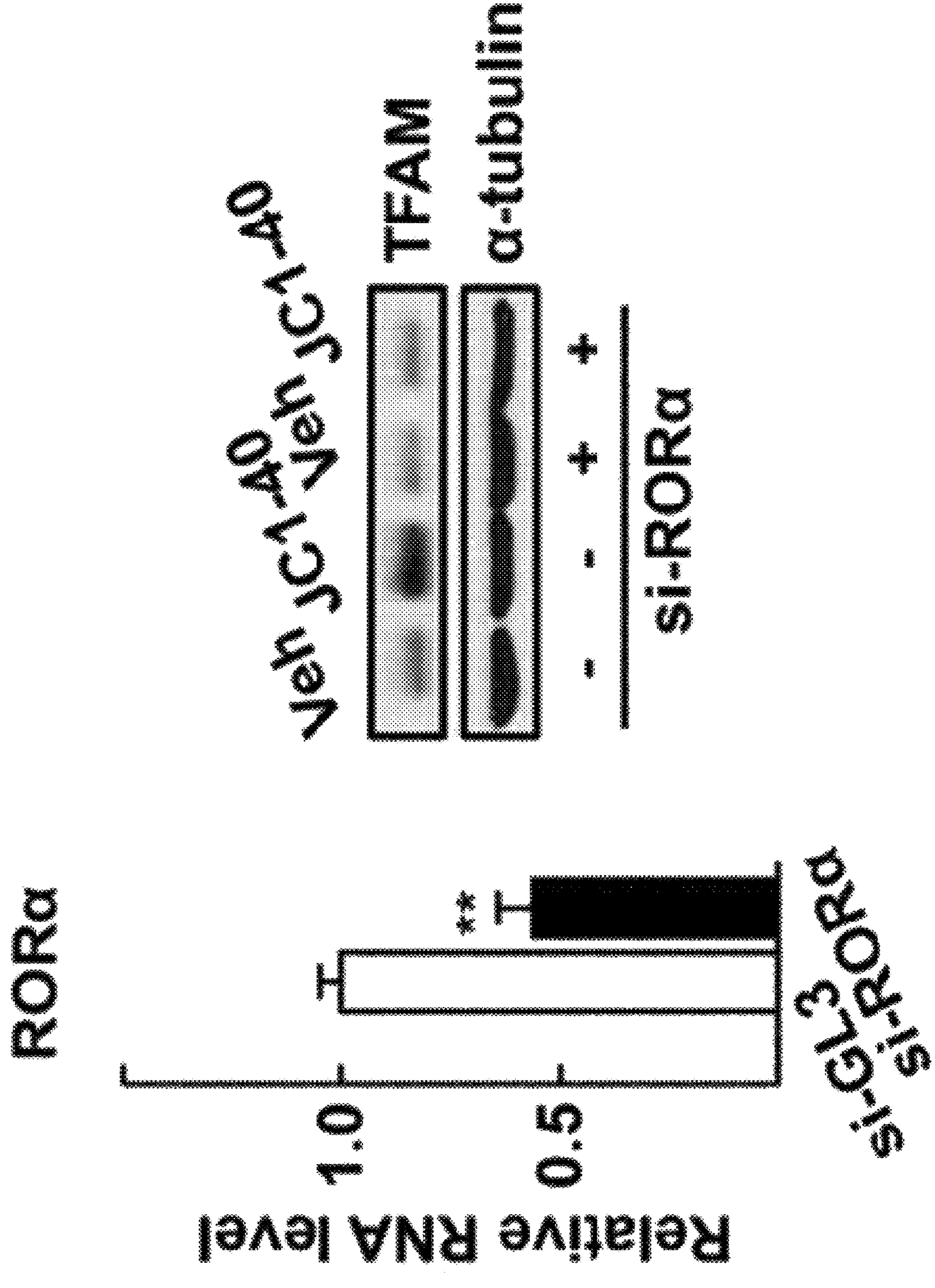
FIG. 5 shows the results confirming whether the JC1-40-induced increase in TFAM expression in C2C12 cells is dependent on RORα.

As shown in FIG. 5, when treated with JC1-40, the protein expression of TFAM, a regulator of mitochondrial biosynthesis, increased, but the increase in TFAM expression did not occur with si-RORα. Through this, it was confirmed that the increase in TFAM expression by JC1-40 is RORα-dependent.

Figure 6A:
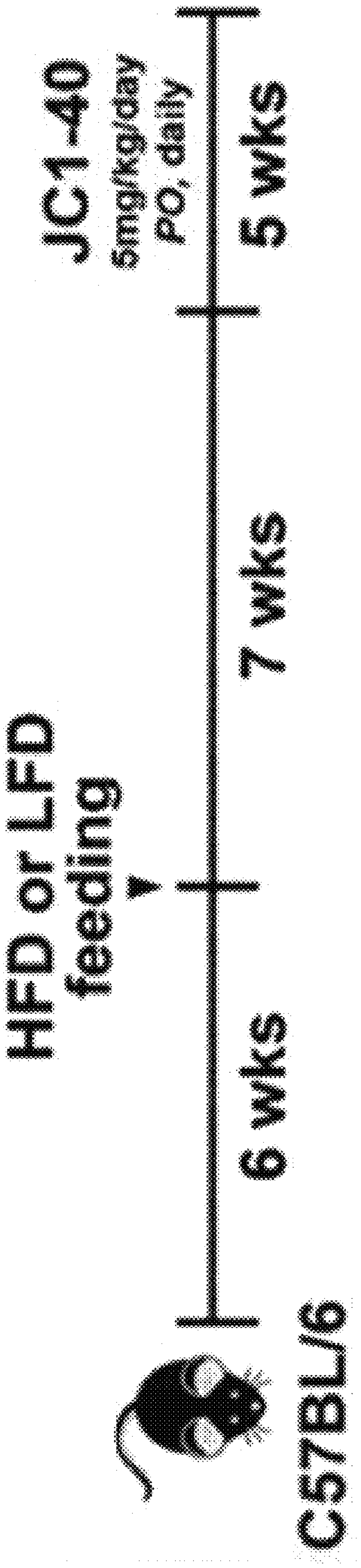
FIGS. 6A and 6B show the experimental method and results verifying the impact of JC1-40 on mitochondrial biosynthesis effects in a high-fat diet-induced animal model.

Example 6. Verification of Mitochondrial Biosynthesis Effect of JC1-40 on Muscle Tissue of High Fat Diet-Induced Animal Model To confirm the correlation between the administration of JC1-40, an increase in mitochondrial biosynthesis, and the suppression of sarcopenia, experiments were conducted using a diet-induced animal model. Specifically, male C57BL/6 mice aged 5 weeks were acclimatized in a temperature and humidity-controlled environment for one week and were provided with a high-fat diet (fats derived from lard and soybean oil, 60 kcal % included, Research diets) for 12 weeks. From the 8th week of the diet, JC1-40 was orally administered once a day for 5 weeks at a concentration of 5 mg/kg (FIG. 6A). In detail, an amount of JC1-40 corresponding to the final concentration was measured and added to sterile water containing 0.5% carboxymethyl cellulose, and then uniformly suspended using a mortar and pestle to produce the drug. The dose for each mouse subject was taken and orally administered using a SONDE®. The control group was administered sterile water containing 0.5% carboxymethyl cellulose in the same manner. After 12 weeks of diet were completed, the mice were anesthetized, the gastrocnemius tissue was extracted, and it was fixed using a 4% paraformaldehyde solution. The fixed tissue underwent washing, decalcification, and dehydration, and was ultimately made into a paraffin block using paraffin. The created paraffin block was cut into sections with a thickness of 3 μm, and after creating sections, protein expression was confirmed with fluorescence using specific antibodies for COX4 (Cytochrome c oxidase subunit 4, Santa Cruz Biotechnology) and TFAM (Mitochondrial transcription factor A, Santa Cruz Biotechnology). The results are shown in FIG. 6B.

Figure 6B:
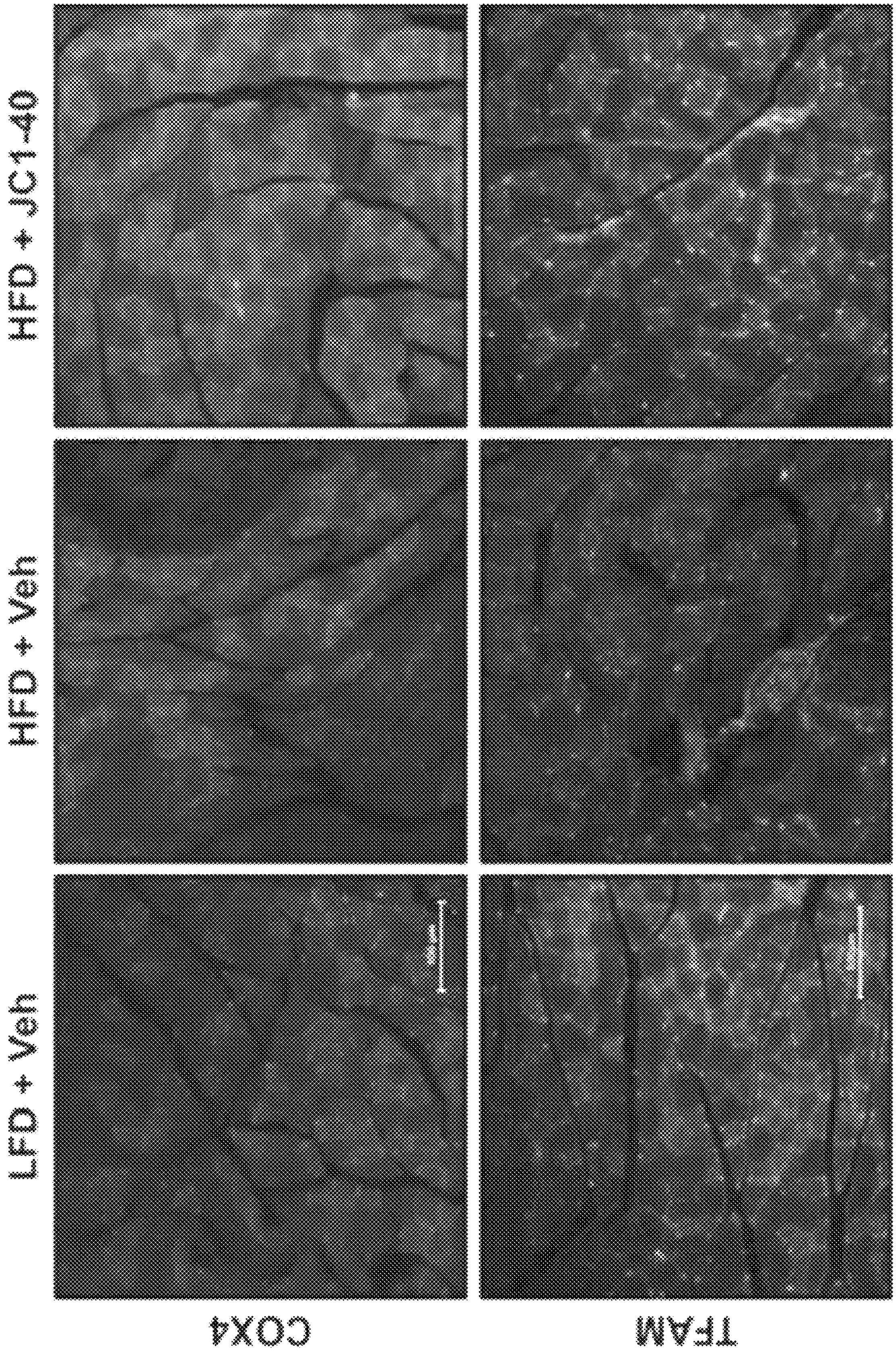

As shown in FIG. 6B, sarcopenia was induced by the high-fat diet. Additionally, in the case where JC1-40 was orally administered, the protein expression of COX4, a mitochondrial component, and TFAM, a regulator of mitochondrial biosynthesis, significantly increased, and it was confirmed that sarcopenia was significantly improved. This means that the sarcopenia inhibitory effect of JC1-40 is excellent.

The description of the present invention as stated above is for illustrative purposes only, and a person having ordinary skill in the art to which the present invention pertains will understand that the technical idea or essential characteristics of the present invention can be easily modified into other specific forms without changing them. Therefore, the examples described above should be understood as illustrative in all aspects and not limited.

INDUSTRIAL APPLICABILITY

The composition comprising JC1-40 as an active ingredient in the present invention may increase mitochondrial membrane potential and enhance the quantity of mitochondria, as well as augment the expression or activity of genes or proteins related to the mitochondria, whereby it may increase mitochondrial biosynthesis. Therefore, it may be utilized for the prevention, improvement, and treatment of sarcopenia, demonstrating industrial applicability.

The invention claimed is:

1. A method of treating obese sarcopenia, comprising the step of administering a composition comprising JC1-40 or a pharmaceutically acceptable salt thereof as an active ingredient to a subject having obese sarcopenia.

2. The method of claim 1, wherein the JC1-40 is an activator of RORα protein.

3. The method of claim 1, wherein the JC1-40 is comprised at a concentration of 1 to 100 μM relative to the total composition.

4. The method of claim 1, wherein the JC1-40 satisfies at least one of the following:

a) increasing mitochondrial membrane potential;

b) increasing mitochondrial quantity; and c) increasing mitochondrial biosynthesis.

5. The method of claim 1, wherein the JC1-40 increases the expression or activity of a gene or protein selected from the group consisting of SDHA, COX5A, MCAD, PGC-1α, NRF1, NRF2α, and TFAM.

6. The method of claim 5, wherein the expression of the TFAM gene or protein is dependent on RORα.

7. A method of increasing mitochondrial biosynthesis, comprising the step of administering a composition comprising JC1-40 or a pharmaceutically acceptable salt thereof as an active ingredient to a subject having obese sarcopenia.

* * * * *